United States Patent [19]

Cooper

[11] Patent Number: 4,988,361

[45] Date of Patent: Jan. 29, 1991

[54] TURNTABLE FOR ARTIFICIAL LIMB

[75] Inventor: John E. Cooper, Leatherhead, England

[73] Assignee: JE Hanger & Company Limited, United Kingdom

[21] Appl. No.: 374,976

[22] Filed: Jul. 3, 1989

[30] Foreign Application Priority Data

Jul. 8, 1988 [GB] United Kingdom ............... 8816311
Oct. 27, 1988 [GB] United Kingdom ............... 8825194

[51] Int. Cl.⁵ .............................................. A61F 2/62
[52] U.S. Cl. ...................................... 623/38; 403/26; 403/325
[58] Field of Search ............... 403/111, 312, 322, 325, 403/327; 623/27, 38, 39, 40, 41, 42, 43, 44, 45, 46

[56] References Cited

U.S. PATENT DOCUMENTS

| | | | |
|---|---|---|---|
| 3,272,168 | 9/1966 | Gardner et al. | 623/38 |
| 4,520,512 | 6/1985 | Lehners et al. | 623/39 |
| 4,795,474 | 1/1989 | Horvath | 623/27 |
| 4,865,611 | 9/1989 | Al-Turaiki | 623/38 |

FOREIGN PATENT DOCUMENTS

| | | |
|---|---|---|
| 0157621 | 10/1985 | European Pat. Off. . |
| 0244493 | 11/1987 | European Pat. Off. . |
| 8502536 | 6/1985 | PCT Int'l Appl. . |
| 185173 | 8/1922 | United Kingdom . |
| 255190 | 7/1926 | United Kingdom . |
| 2155790 | 10/1985 | United Kingdom . |
| 2181060 | 9/1986 | United Kingdom . |
| 2199366 | 12/1987 | United Kingdom . |

*Primary Examiner*—Alan Cannon
*Assistant Examiner*—David H. Willse
*Attorney, Agent, or Firm*—Stevens, Davis, Miller & Mosher

[57] ABSTRACT

A turntable for an artificial limb provides a rotatable joint which enables the limb to be turned into the cross-legged position. The turntable includes two relatively rotatable plates and axially moveable means for locking one plate relative to the other in one position.

16 Claims, 3 Drawing Sheets

TURNTABLE FOR ARTIFICIAL LIMB

This invention relates to a turntable for an artificial limb.

A turntable for a prosthetic leg enables the lower parts of the leg to be released from their normal position so that the wearer can sit cross-legged on the ground. Such turntables are known, but there is a requirement for a simply constructed turntable having, in combination, small axial length and adequate mechanical strength to withstand the static and cyclically variable loads to which the leg is subject.

According to the invention a turntable for releasably interconnecting upper and lower parts of a limb prosthesis to permit the lower part to be rotated from a predetermined normal position, comprises first and second plates, means connecting the plates against movement axially apart, axially moveable means for releasably locking the plates in their normal relative positions, and rolling contact bearing means that fits between the plates adjacent their periphery to permit relative rotation of the plates while maintaining the planes of adjacent faces of the plates parallel.

Preferably the plates are circular in plan with circumferential grooves in their adjoining concealed faces and the rolling contact bearing means is a ball bearing that fits into and spans between the grooves to maintain the plates at a predetermined axial spacing. In this form, the first and second plates preferably have side walls of the same diameter and coaxial with the turntable axis and the ball bearing does not project beyond the surface defined by the side walls.

The means connecting the plates against movement axially apart preferably comprises a connector fastened to the first plate for rotation therewith and connected to the second plate via second rolling contact bearing means. Advantageously the connector and the second rolling contact bearing means fit wholly within the first and second plates. In this form of turntable the connector may be a screw having a shank passing through the second plate and threadedly received in a bore in the first plate, and having a head received in a counterbore in the second plate, and the second rolling contact bearing means may be a ball bearing in the counterbore retained behind the head.

The means for releasably locking the plates in their normal relative positions may comprise a plunger located in one plate and movable axially so as to be engageable with a socket in the other plate. Preferably, the plunger is spring-urged into the plate-locking position and push-button-operated means is provided to move the plunger axially to an unlocking position relative to the said other plate. The push-button is preferably movable radially inwardly with respect to the plates to operate a wedge member engageable with the plunger so as to move the plunger towards the unlocking position, and the push-button is spring-urged radially outwardly so as to tend to operate the wedge member to release the plunger from the unlocking position.

Alternatively, the means for releasably locking the plates in their normal relative positions may comprise a spring-loaded latching lever pivoted to one of the plates for oscillation in a radial plane and snap-engageable in a catch in the other of the plates.

The first and second plates advantageously have connection formations enabling them to be connected by connecting means e.g. screw or bolt means, to upper and lower parts of an endoskeletal limb. Thus in a preferred form, one of the plates has fixing holes disposed in a pattern thereon and opening to the accessible face thereof, said one plate having counterbores from its blind face registering with access holes in the other plate for reception of screws or bolts with their heads in the counterbores and with their stems protruding through the fixing holes; the other plate having at least one access hole rotatable into register with the counterbores to give access thereto, and may also have screw-threaded fixing holes disposed in a pattern staggered with respect to the or each access hole.

Two embodiments of the invention will now be described by way of example only, with reference to the accompanying drawings, in which.

Figure 1:
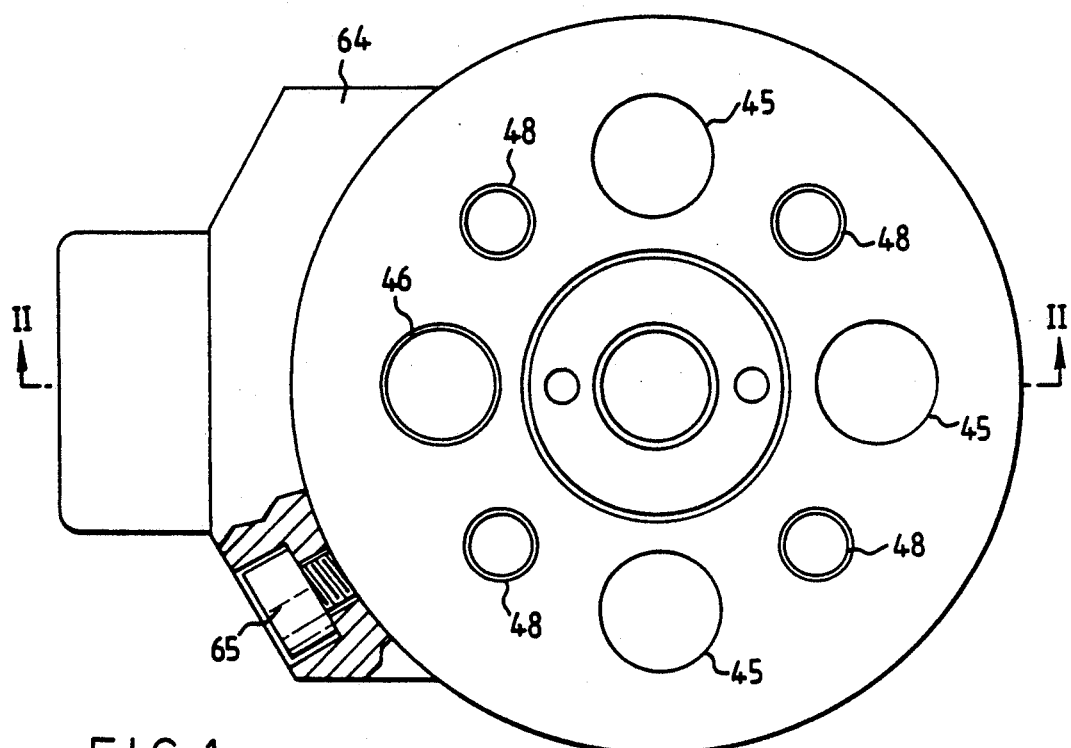
FIG. 1 is a plan view, partly in section, of a turntable for an endoskeletal leg prosthesis according to the first embodiment, viewed from underneath.
Figure 2:
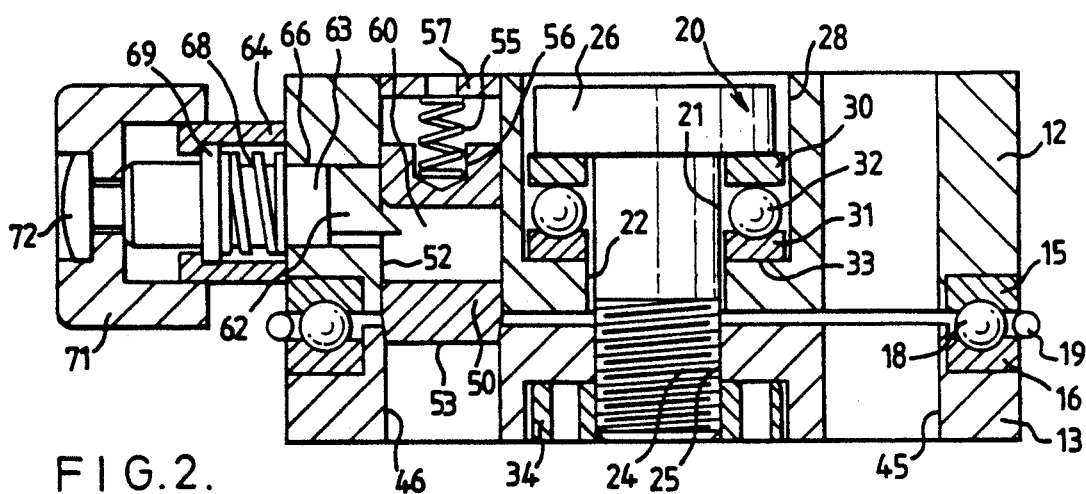
FIG. 2 is a section on the line II—II of FIG. 1 but shown in the upright orientation.
Figure 3:
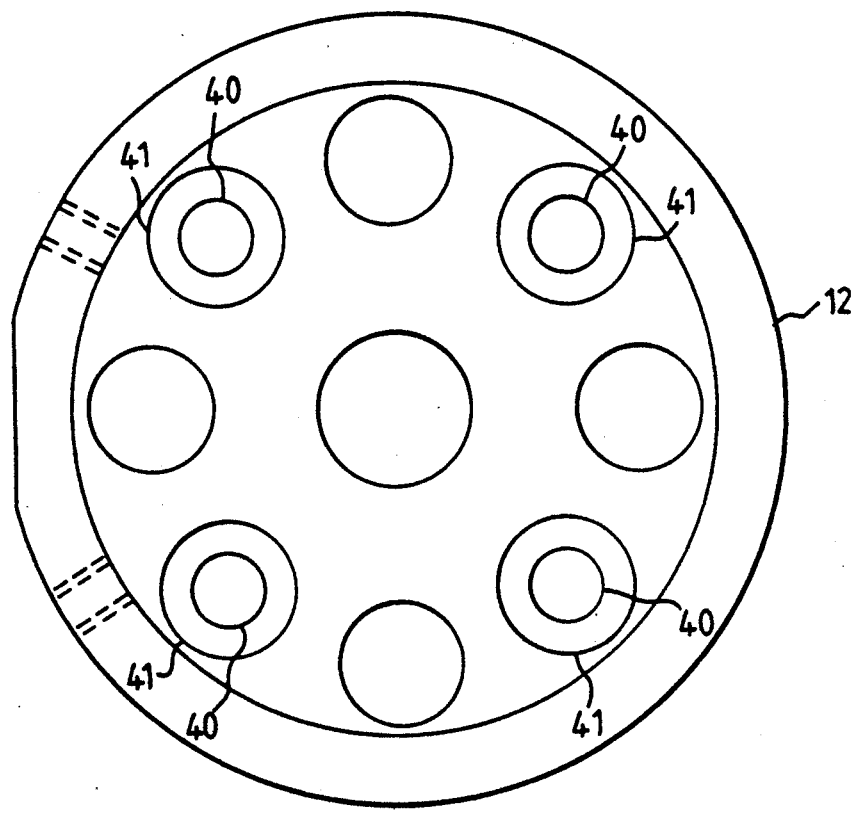
FIG. 3 is an underneath view of an upper plate of the turntable of FIG. 1.

As shown in FIGS. 1–3 the first embodiment of a turntable for a leg prosthesis has a first plate forming an upper plate 12 and a second plate forming a lower plate 13 which are both circular in plan and are positioned at a small clearance one over another in axial alignment. The peripheries of the adjacent faces of plates 12, 13 are relieved, respectively, to receive outer races 15, 16 and balls 18 of a first rolling contact bearing that permits relative rotation of the plates 12, 13 while maintaining the spacing thereof. An O-ring seal 19 is fitted around the outer periphery of the bearing. Since the balls 18 through which compressive loads pass are distanced from the turntable axis, they can resist significant off-axis loads and moments. The plates 12, 13 are connected together by a bolt 20 whose shank 21 passes through a plain bore 22 in the upper plate 12 and whose threaded portion 24 engages into a threaded axial bore 25 through the lower plate 13, the head 26 of the bolt 20 fitting into a larger diameter counterbore 28 in the upper plate 12. Top and bottom inner races 30, 31 and balls 32 defining a second rolling contact bearing fit between the head 26 of the bolt 20 and the blind end 33 of the counterbore. The lower plate 13 and the bolt 20 are locked together by a locknut 34 and are free to rotate as a unit relative to the upper plate 12. The bearing defined by races 30, 31 and balls 32 serves two purposes—firstly it reacts to the compressive load on the bolt head 26 through tightening of the bolt to a predetermined torque to hold the upper and lower plates 12, 13 together, and secondly it provides a low friction bearing permitting the head of the bolt 20 to rotate relatively to the upper plate 12 without it tending to work loose from the lower plate 13. The relatively small diameter of the second rolling contact bearing is not detrimental because it is subject mainly to axial load.

The upper plate 12 has a pattern of four fixing holes 40 opening to the lower face and each having a respective larger diameter counterbore 41 from its lower face. The heads of cap screws (not shown) for connecting the upper plate 12 to upper parts of the leg or to a stump socket connector fit into the counterbores 41 and their shanks project upwardly through the fixing holes 40 for reception in correspondingly positioned threaded holes in the leg upper part or socket connector. The lower plate 13 is formed with a pattern of through holes 45 and 46 of relatively large diameter (the hole 46 is slightly smaller and positioned at a slightly greater radius from the axis than the holes 45). For assembly purposes, as the plates 12, 13 are relatively rotated, the holes 45 and 46 can be arranged to overlie the counterbores 41 to enable the cap screws to be inserted through the upper plate and tightened by means of a hexagonal key. It will be appreciated that other forms of screw or bolt fastening can also be used, with the head of the screws or bolts being recessed in appropriately profiled counterbores in the plate 12. The lower plate 13 is formed with a pattern of threaded fixing holes 48 for attachment thereto of lower parts of the leg. The fixing holes 48 are staggered relative to the through holes 45 and 46 as shown.

A locking mechanism for the turntable comprises an axially movable plunger 50 which is a sliding fit in a hole 52 in the upper plate 12, the hole 52 being arranged to register with the hole 46 of the lower plate 13 when the turntable is in the angular position appropriate to normal use of the limb. The leading end 53 of the plunger is tapered and the adjacent end of the hole 46 is chamfered so that the plunger will slide easily into a socket constituted by the adjacent end of the hole 46, which is otherwise of slightly smaller diameter than that of the plunger, enabling the tapered leading end only of the plunger to enter the hole 46 to a sufficient depth to lock the turntable against rotation.

The plunger 50 is urged towards the locking position (shown in FIG. 2) by a compression spring 55 located at one end on a blind axial bore 56 of the plunger and bearing at its other end against a plug 57 press-fitted into the hole 52. A slot 60 through the plunger 50 has an opening the upper edge of which is tapered at 45°, into which a wedge member constituted by a wedge-shaped end 62 of a plunger release pin 63 projects. The release pin 63 is mounted in a housing 64 secured to the upper plate by screws 65 and passes slidably through a hole 66 in the side of the upper plate 12. A compression coil spring 68 bearing at one end against the side of the upper plate 13 and at the other end against a flange 69 on the pin 63 urges the pin 63 towards the retracted position shown in FIG. 2, in which the plunger 50 has moved axially to enter the hole 46. A generally rectangular release button 71 is secured to the release pin 63 by a screw 72 so that radial inward pressure on the button 71 by the wearer forces the release pin inwardly towards the plunger 50, the wedge member 62 engaging the tapered edge of the slot 60 in the plunger to draw the plunger upwardly and disengage it from the hole 46 thus permitting relative rotation of the upper and lower plates of the turntable.

The through holes 45 in the lower plate are positioned on a pitch circle of diameter such that the plunger 50 will not enter them.

Figure 4:
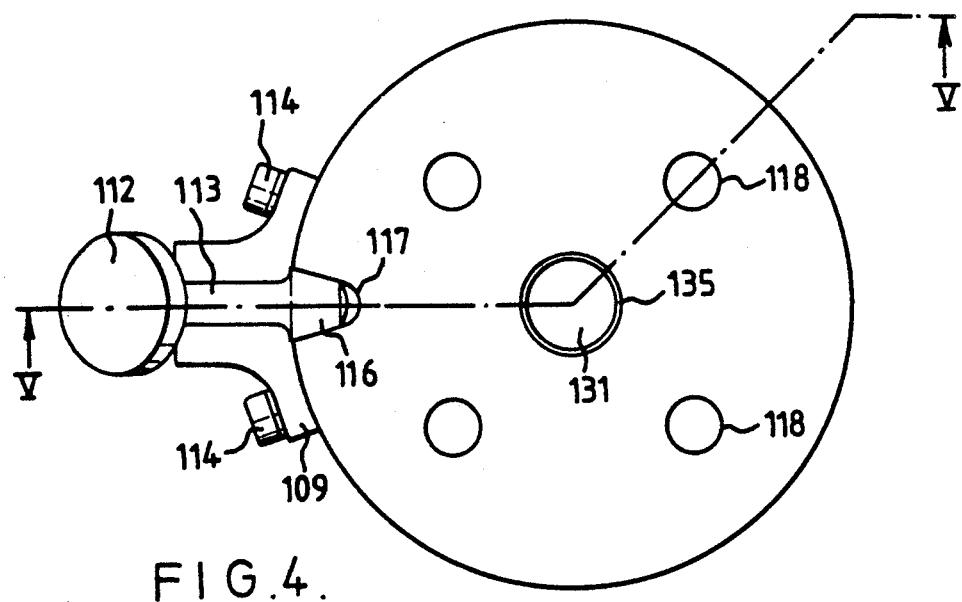
FIG. 4 is a plan view of a turntable for an endoskeletal leg prosthesis according to the second embodiment.
Figure 5:
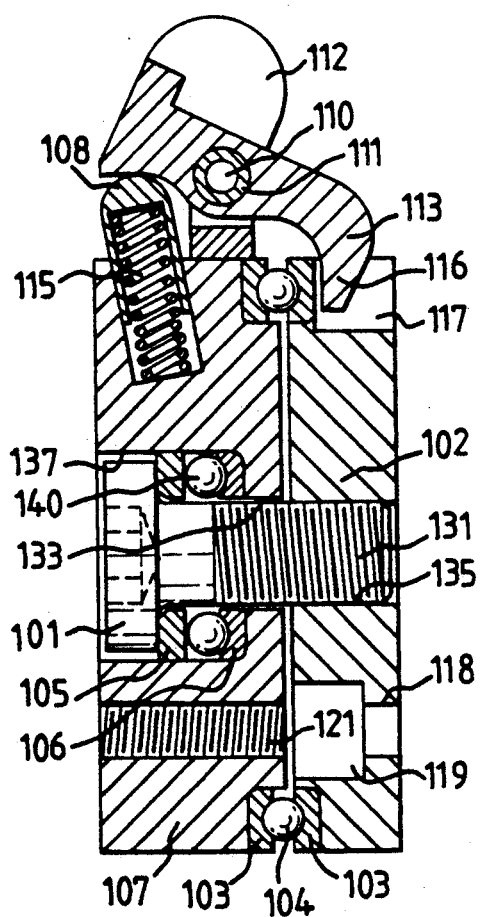
FIG. 5 is a section on line V—V of FIG. 4.
Figure 6:
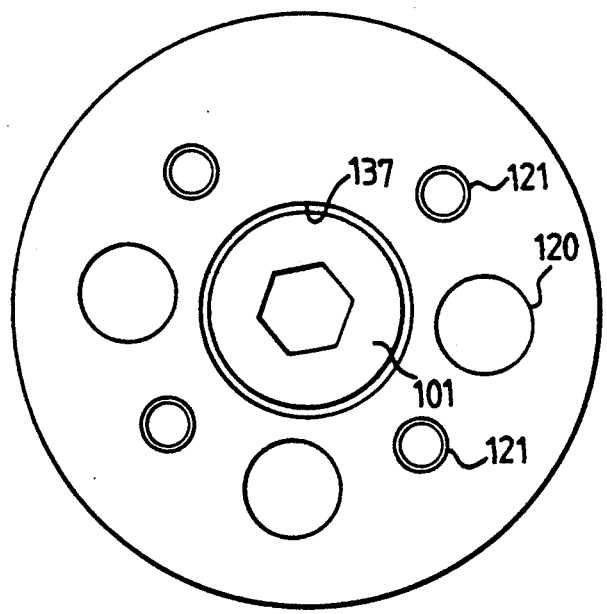
FIG. 6 is an underneath plan view of the turntable of FIG. 4.

As shown in FIGS. 4–6 of the drawings the second embodiment, a turntable for a leg prosthesis, has a top plate 102 and a base plate 107 that are both circular in plan and are positioned at a small clearance one over another in axial alignment. The peripheries of the adjacent faces of plates 102, 107 are relieved to receive outer rings 103 and balls 104 of a first rolling contact bearing that permits relative rotation of the plates 102, 107 while maintaining the spacing thereof. Since the balls 104 through which compressive loads pass are distanced from the turntable axis, they can resist significant off-axis loads and moments. The plates 102, 107 are connected together by a screw 101 whose shank 131 passes through a plain bore 133 in the base plate 107 and engages into a threaded axial bore 135 through the top plate 102 and whose head fits into a larger diameter counterbore 137 in the base plate 107. Top and bottom inner rings 105, 106 and balls 140 defining a second rolling contact bearing fit between the head of the screw 101 and the blind end of the counterbore. In this way the top plate 102 and the screw 101 rotate as a unit relative to the base plate 107. The bearing defined by rings 105, 106 and by balls 140 serves two purposes—firstly it reacts the compressive load on the screw head through tightening of the screw to its predetermined torque to hold the top and bottom plates 102, 107 together, and secondly it provides a low friction bearing permitting the head of the bolt 101 to rotate relatively to the base plate 107 without it tending to work loose from the top plate 102. The relatively small diameter of the second rolling contact bearing is not detrimental because it is subject mainly to axial load.

The lower plate 107 carries a lock bracket 109 fastened thereto by screws 114 and connected by a pin 110 and bush 111 to a locking lever 113. A plunger 108 is a sliding fit in a generally radial but slightly upwardly inclined bore in the base plate 107 and is biased by a compression coil spring 115 against one side of the locking lever 113. The lever 113 can be actuated by finger pressure in a button 112 connected to it to cause it to rotate on the pin 110 to disengage its in-turned head 116 from a catch-defining socket 117 in the periphery of the top plate 102. When the head 116 is withdrawn from the socket 117, the plates 102, 107 can be relatively rotated and the head 116 rides on the side of the top plate 102 until the socket 117 is returned into alignment therewith, at which time the compression coil spring 115 snaps the head 116 back into the socket 117.

The top plate 102 has a pattern of four fixing holes 118 opening to the top face and each having a respective larger diameter counterbore 119 from its lower face. The head of a cap screw 119 for connecting the top plate 102 to upper parts of the leg or to a stump socket connector fits into the counterbore 119 and its shank projects upwardly through the fixing hole 118 for reception in a correspondingly positioned threaded hole in the leg upper part or socket connector. The base plate 107 is formed with a pattern of through access holes 120 of relatively large diameter. As the plates 102, 107 are relatively rotated, the holes 120 can be registered, in this embodiment, aligned, with the counterbores 119 to enable the cap screws to inserted and tightened by means of a hexagonal key. It will be appreciated that other forms of screw or bolt fastening can also be used, with the head of the screw or bolt being concealed in an appropriately profiled counterbore in the plate 102. The plate 107 is also formed with a pattern of threaded fixing holes 121 for attachment thereto of lower parts of the leg. The fixing holes 121 are skew to the access holes 120 as shown.

The two embodiments of turntable described above combine mechanical strength and short axial length with low force needed to effect rotation.

I claim:

1. A turntable for releasably interconnecting upper and lower parts of a limb prosthesis to permit the lower part to be rotated from a predetermined normal position, comprising first and second plates, movable means capable of movement at least partially in the axial direction for releasably locking the plates in their normal relative position, first rolling contact bearing means that fits between the plates adjacent their peripheries to permit relative rotation of the plates while maintaining the planes of adjacent faces of the plates parallel and a connector for connecting the plates against movement axially apart fastened to the first plate for rotation therewith and connected to the second plate by a second rolling contact bearing means.

2. A turntable according to claim 1, wherein the plates are circular in plan with circumferential grooves in their adjoining concealed faces and the first rolling contact bearing means is a ball bearing that fits into and spans between the grooves to maintain the plates at a predetermined axial spacing.

3. A turntable according to claim 2, wherein the first and second plates have side walls of the same diameter and coaxial with the turntable axis and the ball bearing does not project beyond the surface defined by the side walls.

4. A turntable according to claim 1, wherein the connector and the second rolling contact bearing means fits wholly within the first and second plates.

5. A turntable according to claim 4, wherein the connector is a screw having a shank passing through the second plate and threadedly received in a bore in the first plate, and having a head received in a counterbore in the second plate, the second rolling contact bearing means being a ball bearing in the counterbore retained behind the head.

6. A turntable according to claim 1 wherein the moveable means for releasably locking the plates in their normal relative positions comprises a plunger located in one plate and movable axially so as to be engageable with a socket in the other plate.

7. A turntable according to claim 1, wherein one of the first and second plates has fixing holes disposed in a pattern thereon, and the other of said first and second plates has at least one access hole capable of registering with the fixing holes to give access for fixing means thereto.

8. A turntable according to claim 7, wherein said other plate has fixing holes spaced apart around the circumference of a circle concentric with the rotational axis and disposed in a pattern staggered with respect to said at least one access hole.

9. A turntable for releasably interconnecting upper and lower parts of a limb prosthesis to permit the lower part to be rotated from a predetermined normal position comprising first and second plates, means connecting the plates against movement axially apart, a plunger located in one plate capable of movement at least partially in the axial direction so as to be engageable with a socket in the other plate thereby releasably locking the plates in their normal relative position, a radially movable member engageable with the plunger to move the plunger towards the unlocking position, and rolling contact bearing means that fits between the plates adjacent their peripheries to permit relative rotation of the plates while maintaining the planes of adjacent faces of the plates parallel.

10. A turntable according to claim 9 wherein the radially movable member includes a wedge member.

11. A turntable according to claims 10 wherein a push-button is provided to enable radially inward pressure to be applied to the wedge member so as to unlock the turntable, spring means being provided to urge the wedge member radially outwardly.

12. A turntable according to claim 9 wherein spring means is provided to urge the plunger into the plate locking position.

13. A turntable for releasably interconnecting upper and lower parts of a limb prosthesis to permit the lower part to be rotated from a predetermined normal position, comprising first and second plates, means connecting the plates against movement axially apart, a spring loaded latching lever pivotally attached to one of the plates for rotation in a radial plane and snap-engageable in a catch in the other of the plates for releasably locking the plates in their normal relative position, and rolling contact bearing means that fits between the plates adjacent their peripheries to permit relative rotation of the plates while maintaining the planes of adjacent faces of the plates parallel.

14. A turntable according to claim 12 wherein one of said first and second plates has fixing holes disposed in a pattern thereon, and the other of said first and second plates has at least one access hole capable of registering with the fixing holes to give access for fixing means thereto.

15. A turntable according to claim 13 wherein said other plate has fixing holes spaced apart around the circumference of a circle concentric with the rotational axis and disposed in a pattern staggered with respect to said at least one access hole.

16. A turntable according to claim 6 wherein spring means is provided to urge the plunger into the plate-locking portion.

* * * * *